United States Patent
Carney et al.

(10) Patent No.: US 6,254,606 B1
(45) Date of Patent: Jul. 3, 2001

(54) LASER AIMING DEVICE FOR PERFORMING ANTERIOR CRUCIATE LIGAMENT RECONSTRUCTION SURGERY AND METHOD FOR USING SAME

(76) Inventors: William P. Carney; Rita D. Carney, both of 57 Emerson Rd., Glen Rock, NJ (US) 07452

( * ) Notice: Subject to any disclaimer, the term of this patent is extended or adjusted under 35 U.S.C. 154(b) by 0 days.

(21) Appl. No.: 09/416,876

(22) Filed: Oct. 13, 1999

(51) Int. Cl.[7] ................................................... A61B 17/58

(52) U.S. Cl. ............................ 606/102; 606/96; 606/98; 606/179

(58) Field of Search ................................ 606/86, 87, 96, 606/97, 98, 102, 179

(56) References Cited

U.S. PATENT DOCUMENTS

| | | | | |
|---|---|---|---|---|
| 5,163,940 | * | 11/1992 | Bourque | 606/96 |
| 5,562,664 | * | 10/1996 | Durlacher et al. | 606/96 |
| 5,613,971 | * | 3/1997 | Lower et al. | 606/96 |
| 5,643,273 | * | 7/1997 | Clark | 606/96 |
| 5,968,050 | * | 10/1999 | Torrie | 606/87 |
| 6,120,511 | * | 9/2000 | Chan | 606/96 |

* cited by examiner

*Primary Examiner*—Pedro Philogene
(74) *Attorney, Agent, or Firm*—Jean-Marc Zimmerman

(57) ABSTRACT

An apparatus and method using a laser in conjunction with a conventional tibial aiming device for assisting a surgeon in drilling collinear tibial and femoral tunnels during ACLR surgery. The laser is used to determine the angle at which to drill the tibial tunnel with respect to a femoral reference point selected by the surgeon so that the tunnels are collinear.

20 Claims, 4 Drawing Sheets

LASER AIMING DEVICE FOR PERFORMING ANTERIOR CRUCIATE LIGAMENT RECONSTRUCTION SURGERY AND METHOD FOR USING SAME

FIELD OF THE INVENTION

The present invention pertains to anterior cruciate ligament reconstruction (ACLR) surgery, and more particularly to an improved device and method for performing such surgery.

BACKGROUND OF THE INVENTION

The anterior cruciate ligament (ACL) spans the knee, joining the femur bone of the upper leg and the tibia bone of the lower leg. The ACL enables the knee to bend so that the leg below the knee can move in relation to the leg above the knee. Injuries to the ACL are very common, especially among athletes.

When the ACL is torn it can not be directly repaired with a suture, but must instead be reconstructed using grafted donor tissue which is placed across the knee in the same position and orientation as the ACL it replaces through two tunnels, one drilled in the tibia and the other in femur. To ensure proper range of motion of the reconstructed knee, the tunnels should be collinear. At present, a conventional tibial aiming device, shown in FIG. 1 and described in more detail below, is used to assist a surgeon in determining the proper angle at which the tunnels should be drilled through reference points selected on the tibia and femur, respectively, so that the tunnels are collinear.

Conventional tibial aiming devices suffer from a significant drawback. Specifically, they rely upon the eyes of a surgeon to determine the angle at which the tunnels should be drilled with respect to the aforementioned reference points. However, relying upon one's eyesight to estimate this angle often results in tunnels that are not collinearly formed and thus an improperly reconstructed ACL.

SUMMARY OF THE INVENTION

An apparatus and method using a laser in conjunction with a conventional tibial aiming device for assisting a surgeon in drilling collinear tibial and femoral tunnels during ACLR surgery. The laser is used to determine the angle at which to drill the two tunnels with respect to tibial and femoral reference points selected by the surgeon so that the tunnels are collinear.

DETAILED DESCRIPTION OF THE DRAWINGS

Figure 1:
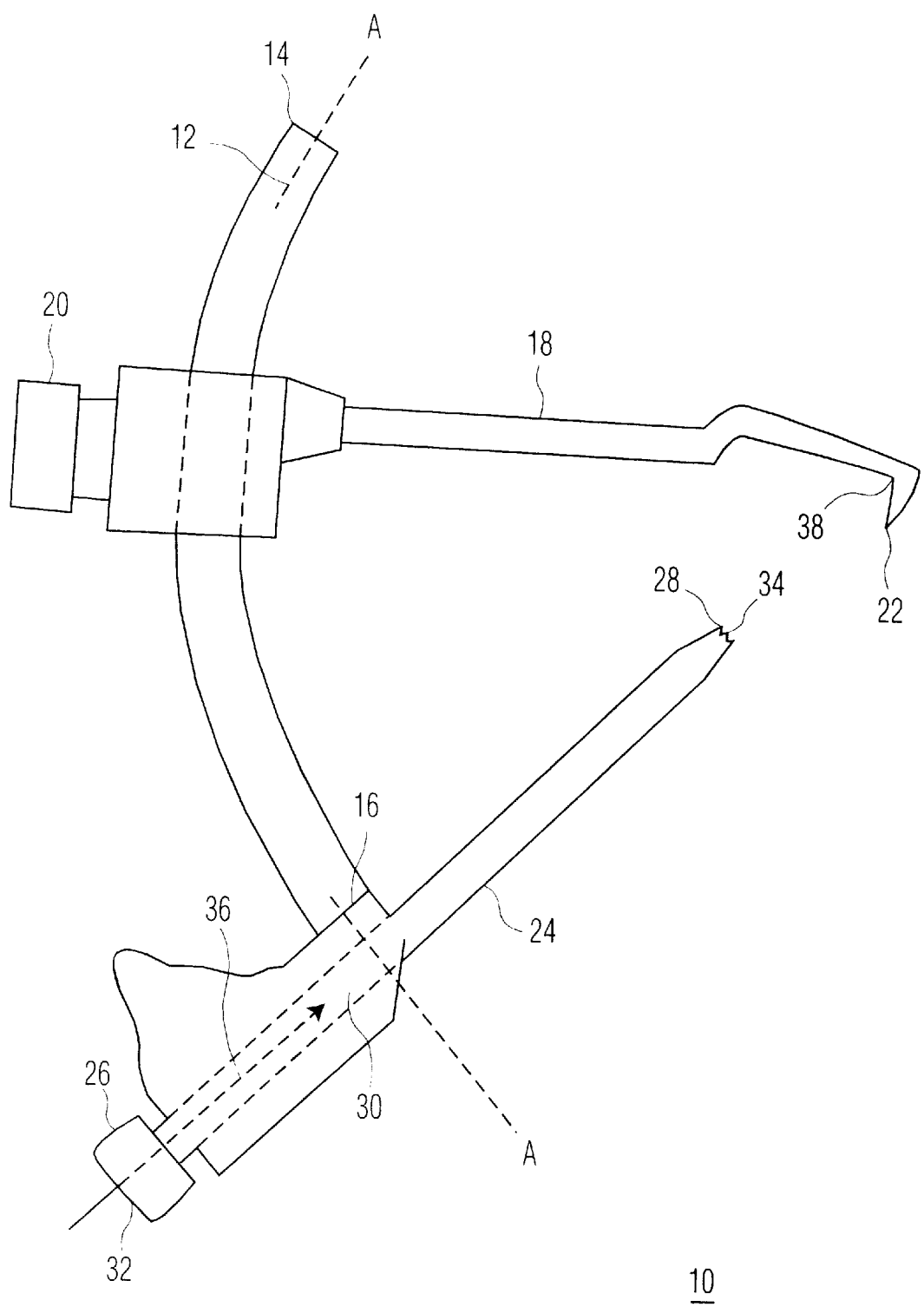
FIG. 1 shows a conventional tibial aiming device for assisting a surgeon in drilling collinear tibial and femoral tunnels during ACLR surgery.

FIG. 1 shows a conventional tibial aiming device 10. Since the present invention incorporates device 10, a detailed review of its operation will aid in understanding the teaching of the present invention. Device 10 includes an arc-shaped element 12 having a first end 14 and an oppositely disposed second end 16, a first arm 18 having an adjustable screw first end 20 and an oppositely disposed finger-shaped second end 22, and a second arm 24 having adjustable screw first end 26 and an oppositely disposed jagged edge-shaped second end 28.

Second arm 24 includes a channel 30 having openings 32 and 34 disposed between ends 26 and 28, respectively. A guide wire 36 for drilling the tibial tunnel is deployed through channel 30, being inserted through opening 32 and exiting through opening 34. Adjustable screw first end 20 can be selectively loosened to enable first arm 18 to be slidably moved along axis A—A of arc-shaped element 12. Similarly, adjustable screw first end 26 can be selectively loosened to enable jagged edge-shaped second end 28 to be extended away from first end 26 in relation to axis A—A. Elbow 38 and jagged edge-shaped second end 28 are collinear with one another.

Figure 2:
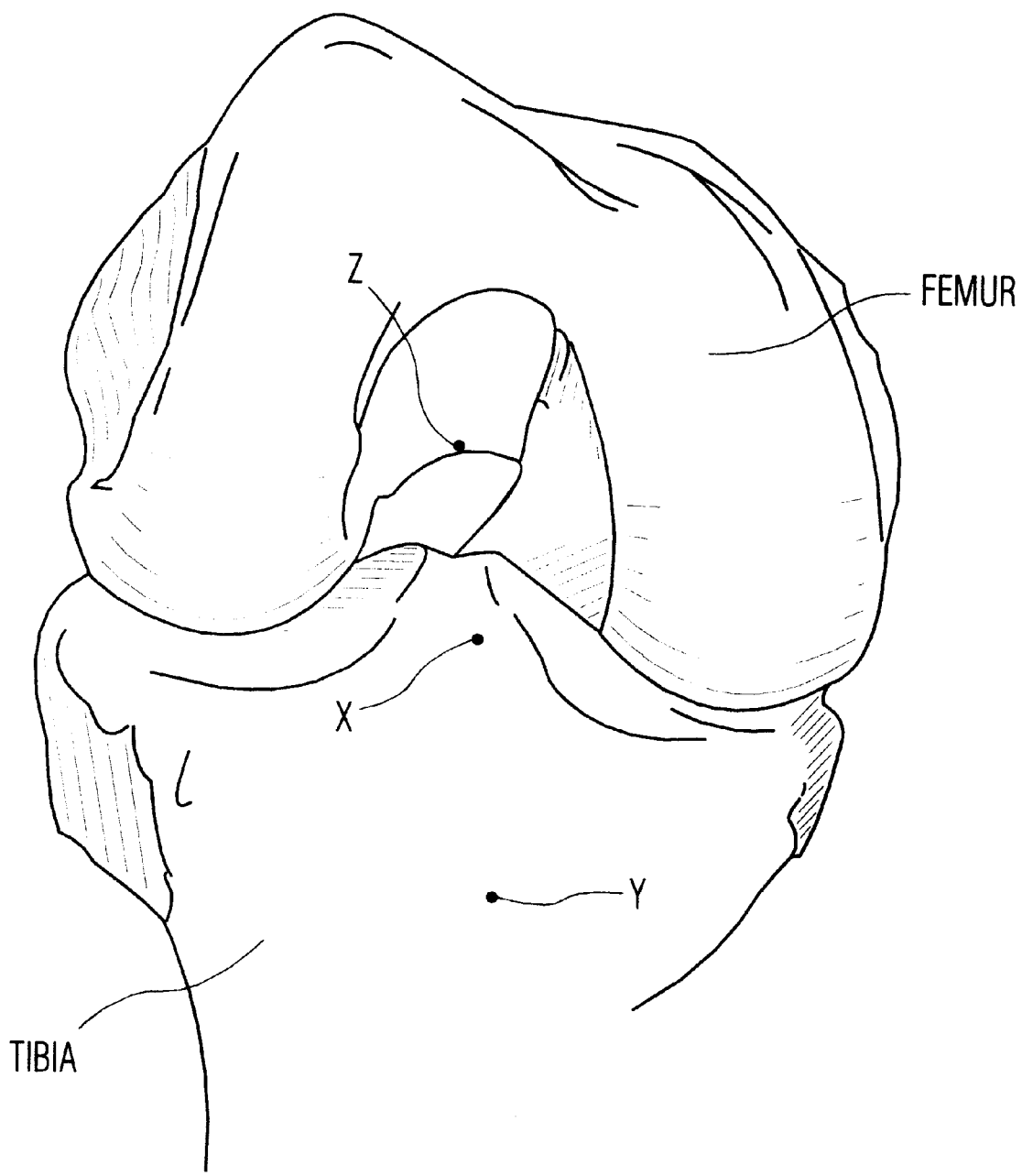
FIG. 2 shows a knee and reference points on both the tibia and femur bones, respectively, through which two tunnels are drilled during ACLR surgery.

To use device 10, a surgeon selects a reference point X, shown in FIG. 2, inside the knee on the top surface of the tibia at which the tibial tunnel is to terminate. Using adjustable screw ends 20 and 26, arms 18 and 24, respectively, are moved to secure device 10 to the tibia with finger-shaped second end 22 resting atop reference point X and jagged edge-shaped second end 28 positioned adjacent a reference point Y, shown in FIG. 2, located on a side of the tibia. Reference point Y is positioned below reference point X. The angle at which ends 22 and 28 are secured to the tibia and thus the angle at which guide wire 38 is deployed and the tibial tunnel is drilled are determined with reference to a corresponding reference point Z, also shown in FIG. 2, selected by the surgeon on the femur bone and at which the femoral tunnel is to be drilled. The angle is selected so that the two tunnels will be drilled collinearly. At present, a surgeon estimates this angle using his or her eyesight.

Once finger-shaped second ends 22 and jagged edge-shaped second end 28 are secured to the tibia, guide wire 36 is deployed through channel 30 and drilled into the tibia at reference point Z. A cannulated reamer is then inserted through opening 32 into channel 30 and drilled along the guide wire upwards through the tibia from reference point Y to reference point X to form the tibial tunnel. Once the tibial tunnel is formed, the guide wire is deployed from reference point X and drilled into reference point Z on the femur. The cannulated reamer is then drilled along the guide upwards through the femur to form the femoral tunnel. Once the tibial and femoral tunnels are formed, the guide wire and cannulated reamer are withdrawn through the respective tunnels and through channel 30, and the graft is inserted through the tibial and femoral tunnels and secured to the tibia and femur bones by means of securing pins, screws or the like.

Figure 3:
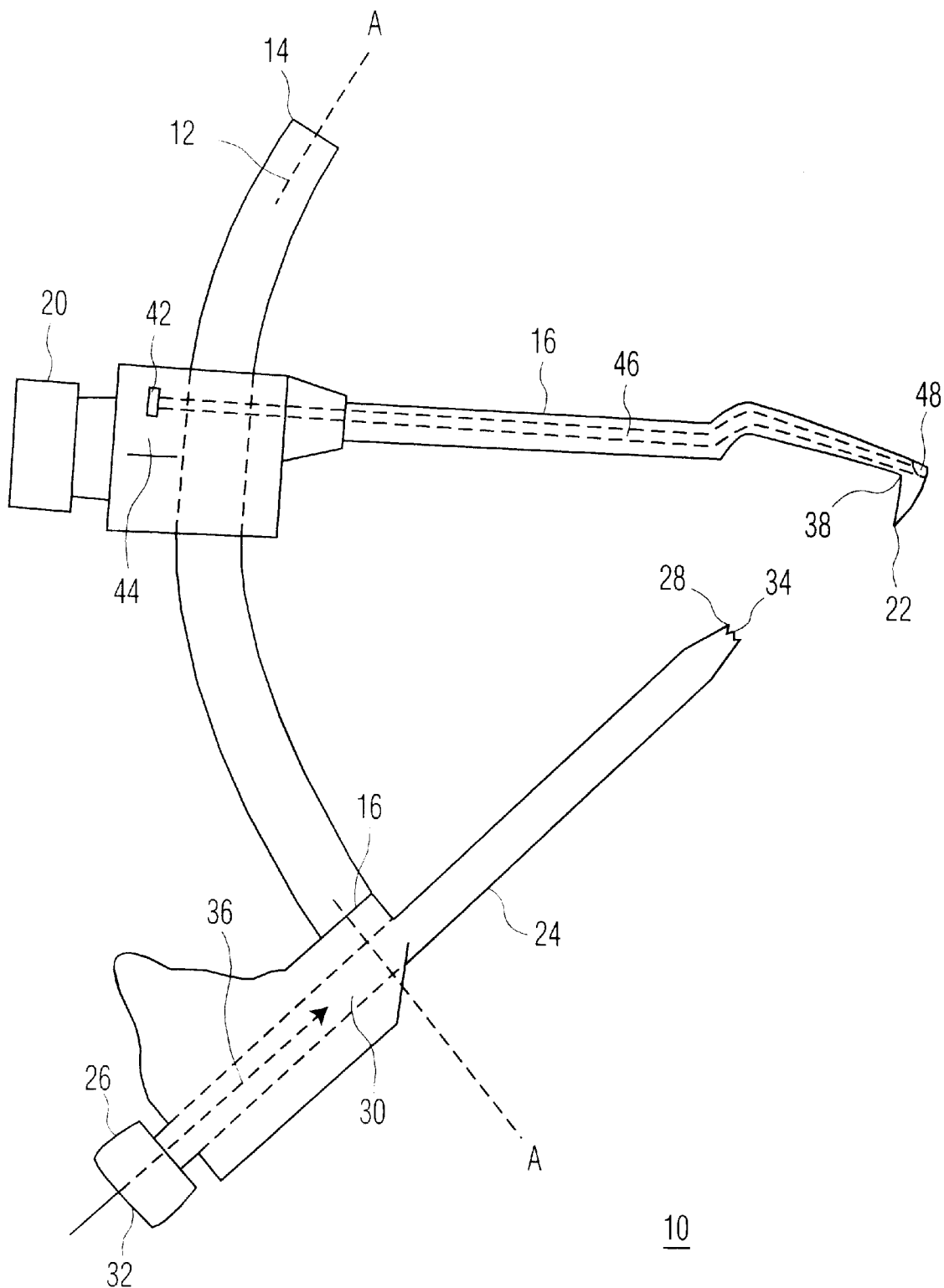
FIG. 3 shows an exemplary embodiment of a tibial aiming device including a laser according to the present invention.

FIG. 3 shows an exemplary embodiment of an improved tibial aiming device 40 according to the present invention. Since device 40 incorporates all of the components of conventional tibial aiming device 10, components in FIG. 3 having the same function as those shown in FIG. 1 are designated by the same number. Device 40 also includes a high intensity light source 42 housed in a module 44 coupled to device 10 and a fiber optic cable 46 positioned inside of first arm 18 and terminating at an opening 48 oppositely disposed from finger-shaped second end 22 and through which light from high intensity light source 42 is projected from tibial reference point X to femoral reference point Z. Alternatively, fiber optic cable need not be positioned inside of first arm 18, but can instead be secured along the exterior of first arm 18.

High intensity light source 42 can be a laser, a light emitting diode or any other light source. In addition, light source 42 can be selectively turned on and off by a surgeon. The angle at which high intensity light source 42 projects light through opening 48 can be adjusted by a surgeon so that guide wire 38 will be deployed at such an angle that the tibial tunnel to be drilled will be collinear with the femoral tunnel to be drilled. Device 40 enables the angle at which the tibial tunnel is to be drilled with respect to the femoral reference point so that the tibial and femoral tunnels are collinear to be determined more exactly and more easily than is possible using conventional device 10.

Figure 4:
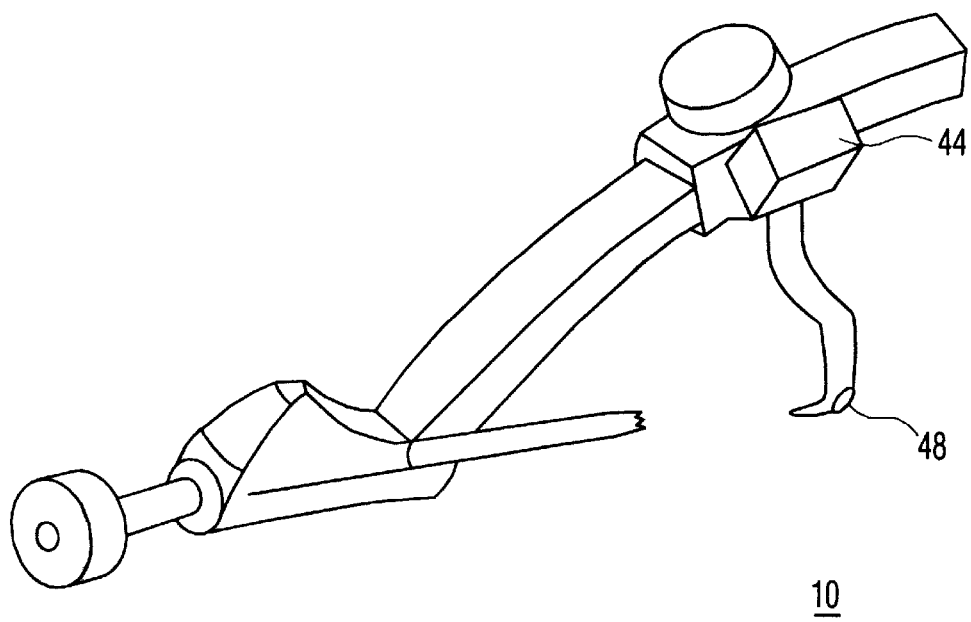
FIG. 4 shows a perspective view of the device shown in FIG. 3.

FIG. 4 shows a perspective view of device 40.

Figure 5:
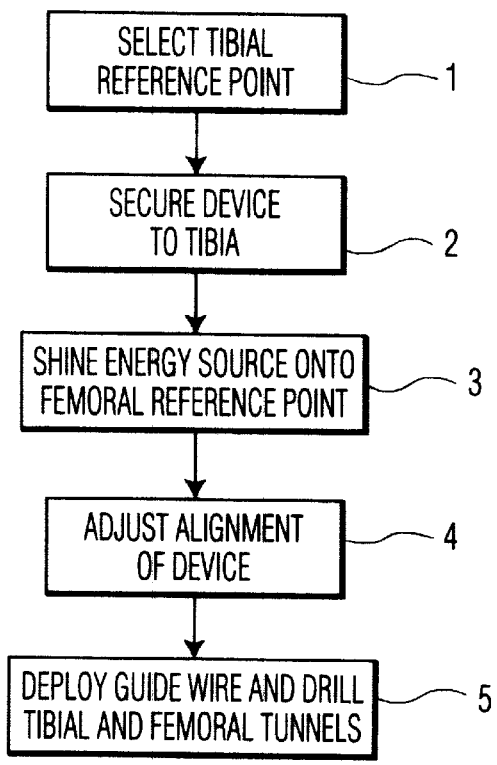
FIG. 5 flowchart depicting the steps in using the tibial aiming device shown in FIG. 3.

FIG. 5 shows a flowchart depicting the steps in the operation of device 40. At step 1, a surgeon selects tibial reference point X. At step 2, the surgeon uses screw ends 20 and/or 26 to adjust arms 18 and 24, respectively, to secure device 40 to the tibia, with finger-shaped second end 22 resting atop reference point X. At step 3, the surgeon turns high intensity energy source 42 on and shines the energy source onto femoral reference point Z. At step 4, the surgeon adjusts the alignment of device 40 so that the angle at which guide wire 38 is deployed and the tibial tunnel is drilled with respect to the femoral reference point Z results in collinear tibial and femoral tunnels being formed. At step 5, the surgeon deploys the guide wire and drills the tibial and femoral tunnels.

In an alternative embodiment of the present invention not shown, an energy source other than high intensity light source 42 can be used. For example, an infrared or acoustic energy source can be used, wherein such alternative embodiments also include sensors at the energy source and on the guide wire for communicating with one another and indicating to the surgeon by audio and/or visual means when an angle has been attained that will enable collinear tibial and femoral tunnels to be drilled.

Numerous modifications to and alternative embodiments of the present invention will be apparent to those skilled in the art in view of the foregoing description. Accordingly, this description is to be construed as illustrative only and is for the purpose of teaching those skilled in the art the best mode of carrying out the invention. Details of the structure and method may be varied substantially without departing from the spirit of the invention and the exclusive use of all the modifications which come within the scope of the appended claims is reserved.

What is claimed is:

1. An improved tibial aiming device for assisting a surgeon in drilling collinear tibial and femoral tunnels during an anterior cruciate ligament reconstruction surgery, wherein the improvement consists of:

a high intensity light source coupled to a tibial aiming device, wherein the high intensity light source enables a surgeon to determine an angle at which a tibial tunnel is drilled with respect to a femoral reference point selected by the surgeon so that the tibial tunnel and a femoral tunnel are collinear.

2. The device according to claim 1, wherein the device includes a first arm adapted for coupling to a top surface of the tibia and a second arm adapted for coupling to a side of the tibia, the first arm including a fiber optic cable through which the high intensity light source is projected.

3. The device according to claim 1, wherein the high intensity light source is housed in a module coupled to the tibial aiming device.

4. The device according to claim 1, wherein the high intensity light source is a laser.

5. The device according to claim 1, wherein the high intensity light source is a light emitting diode.

6. The device according to claim 1, wherein the angle at which the high intensity light source is projected from the device is adjustable.

7. The device according to claim 1, wherein the high intensity light source can be selectively turned on and off.

8. The device according to claim 2, wherein the first arm includes a finger-shaped end adapted for resting atop the tibial reference point, and further includes an opening oppositely disposed to the finger-shaped end through which the high intensity light source is projected to the femoral reference point.

9. A tibial aiming device, comprising a body;

a first arm coupled to the body;

a second arm coupled to the body, the first and seconds arms being adapted for coupling to a tibia bone;

an energy source coupled to the body, wherein the energy source enables a surgeon to determine an angle at which a guide wire is deployed from a tibial reference point selected by a surgeon to a femoral reference point selected by the surgeon so that collinear tibial and femoral tunnels are drilled.

10. The device according to claim 9, wherein the energy source is housed in a module coupled to the body.

11. The device according to claim 9, wherein the energy source is a laser.

12. The device according to claim 9, wherein the energy source is a light emitting diode.

13. The device according to claim 9, wherein the angle at which the energy source is projected from the device is adjustable.

14. The device according to claim 9, wherein the energy source can be selectively turned on and off.

15. The device according to claim 9, wherein the first arm includes a finger-shaped end adapted for resting atop a tibial reference point, and further includes an opening oppositely disposed to the finger-shaped end through which the energy source is projected to the femoral reference point.

16. The device according to claim 9, wherein the energy source is an infrared energy source and the device includes means for informing the surgeon when the desired angle has been attained.

17. The device according to claim 9, wherein the energy source is an acoustic energy source and the device includes means for informing the surgeon when the desired angle has been attained.

18. A method for assisting a surgeon in drilling collinear tibial and femoral tunnels during an anterior cruciate ligament reconstruction surgery, comprising the step of:

directing a high intensity light source from a tibial reference point selected by a surgeon to a femoral reference point selected by a surgeon for determining an angle at which to drill a tibial tunnel with respect to the femoral reference point so that the tibial tunnel is collinear with a femoral tunnel to be drilled.

19. The method according to claim 9, wherein the high intensity light source is a laser.

20. The method according to claim 19, wherein the high intensity light source is coupled to a tibial aiming device.

* * * * *